(12) United States Patent
Wagner et al.

(10) Patent No.: US 9,399,011 B2
(45) Date of Patent: *Jul. 26, 2016

(54) LOW VISCOSITY POLYORGANOSILOXANES COMPRISING QUATERNARY AMMONIUM GROUPS, METHODS FOR THE PRODUCTION AND THE USE THEREOF

(71) Applicant: Momentive Performance Materials GmbH, Leverkusen (DE)

(72) Inventors: Roland Wagner, Bonn (DE); Karl-Heinz Stachulla, Leverkusen (DE); Karl-Heinz Sockel, Leverkusen (DE); Sigfredo Gonzales, Danbury, CT (US)

(73) Assignee: Momentive Performance Materials GmbH, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/387,589

(22) PCT Filed: Mar. 28, 2013

(86) PCT No.: PCT/US2013/034248
§ 371 (c)(1),
(2) Date: Sep. 24, 2014

(87) PCT Pub. No.: WO2013/148935
PCT Pub. Date: Oct. 3, 2013

(65) Prior Publication Data
US 2015/0037273 A1    Feb. 5, 2015

Related U.S. Application Data

(60) Provisional application No. 61/617,173, filed on Mar. 29, 2012.

(51) Int. Cl.
| | |
|---|---|
| *A61K 8/898* | (2006.01) |
| *C08L 83/10* | (2006.01) |
| *C08L 83/12* | (2006.01) |
| *D06M 15/643* | (2006.01) |
| *C08G 59/16* | (2006.01) |
| *C08G 59/30* | (2006.01) |
| *C08G 59/68* | (2006.01) |
| *A61Q 5/00* | (2006.01) |
| *C07F 7/10* | (2006.01) |
| *C08G 77/14* | (2006.01) |
| *C08G 77/388* | (2006.01) |
| *C08G 77/445* | (2006.01) |

(52) U.S. Cl.
CPC . *A61K 8/898* (2013.01); *A61Q 5/00* (2013.01); *C07F 7/10* (2013.01); *C08G 59/1472* (2013.01); *C08G 59/306* (2013.01); *C08G 59/686* (2013.01); *C08L 83/10* (2013.01); *C08L 83/12* (2013.01); *D06M 15/643* (2013.01); *C08G 77/14* (2013.01); *C08G 77/388* (2013.01); *C08G 77/445* (2013.01)

(58) Field of Classification Search
None
See application file for complete search history.

(56) References Cited

U.S. PATENT DOCUMENTS

| | | | | |
|---|---|---|---|---|
| 4,833,225 | A * | 5/1989 | Schaefer | A61K 8/898 424/70.122 |
| 7,964,694 | B2 * | 6/2011 | Ferenz | A61K 8/898 424/122 |
| 2004/0048996 | A1 * | 3/2004 | Lange | A61K 8/898 528/10 |
| 2004/0138400 | A1 * | 7/2004 | Lange | A61K 8/898 528/38 |
| 2006/0163524 | A1 * | 7/2006 | Lange | A61K 8/416 252/8.63 |
| 2007/0106045 | A1 * | 5/2007 | Lange | A61K 8/046 528/29 |
| 2009/0142293 | A1 * | 6/2009 | Wagner | A61K 8/898 424/78.37 |
| 2011/0037012 | A1 * | 2/2011 | Wagner | C08G 77/388 252/8.63 |
| 2015/0056155 | A1 | 2/2015 | Wagner et al. | |
| 2015/0299400 | A1 | 10/2015 | Wagner et al. | |

FOREIGN PATENT DOCUMENTS

| | | |
|---|---|---|
| DE | 10 2005 036602 A1 | 2/2007 |
| WO | 2004/046452 A2 | 6/2004 |
| WO | 2004/090007 A2 | 10/2004 |
| WO | 2009/115412 A1 | 9/2009 |

* cited by examiner

*Primary Examiner* — Robert S Loewe
(74) *Attorney, Agent, or Firm* — Dilworth & Barrese, LLP

(57) ABSTRACT

Low viscosity polyorganosiloxanes comprising a) at least one polyorganosiloxane group, b) at least one quaternary ammonium group, c) at least one terminal ester group, methods of the manufacture thereof and their use for the modification of surfaces of substrates.

20 Claims, No Drawings

LOW VISCOSITY POLYORGANOSILOXANES COMPRISING QUATERNARY AMMONIUM GROUPS, METHODS FOR THE PRODUCTION AND THE USE THEREOF

CROSS-REFERENCE TO RELATED APPLICATIONS

This application claims priority to U.S. Provisional Patent application Ser. No. 61/617,173 filed Mar. 29, 2012.

FIELD OF THE INVENTION

The present invention provides for a polyorganosiloxane having a low viscosity and comprising quaternary ammonium groups and terminal ester groups, methods for the production and use thereof.

BACKGROUND OF THE INVENTION

Silicone quats (silicones containing quaternary ammonium groups optionally containing polyorganosiloxane substituents) are known to be highly substantive. DE 3719086 describes the reaction of $\alpha,\omega$-diepoxides with tertiary amines in the presence of acids yielding $\alpha,\omega$-diquaternary siloxanes. They can be used for hair care purposes. DE 3719086 describes tetra alkyl derivatives as well as aromatic imidazolinium derivatives.

The reaction of $\alpha,\omega$-diepoxides with di-tertiary amines in the presence of acids yields polyloop polyquaternary polyorganosiloxanes (EP-A-282720). The advantage of these materials is an improved wash off resistance from hair.

The reaction of $\alpha,\omega$-diepoxides with dimethylamine in the presence of acids yields polyloop polyquaternary polyorganosiloxanes having one quat group between the siloxane blocks is disclosed in U.S. Pat. No. 6,730,766.

Polyquaternary imidazolinium derivates are described in U.S. Pat. No. 6,240,929. These cationic compounds possess an improved compatibility with anionic surfactants in cosmetic formulations.

The incorporation of alkylene oxide moieties in silicone quats is to further increase the hydrophilicity.

Silicone quats containing quat groups as well as polyethylene oxide moieties in side chains are described in U.S. Pat. Nos. 5,098,979, 5,153,294 and 5,166,297. The substantivity of the materials is relatively low.

Silicone based block copolymers containing quat functions that also include polyether moieties are described in WO 02/10257, WO 02/10259 and US 2002/0103094 A. The alkylene oxide structures are incorporated into the block copolymer as $\alpha,\omega$-difunctional moieties.

U.S. Pat. No. 6,242,554 describes $\alpha,\omega$-difunctional siloxane derivatives containing one polyether and one quat function separated from each other. The substantivity of these monoquats is insufficient.

U.S. Pat. No. 4,921,895 describes blends of polyethersiloxanes and quaternary ammonium groups containing siloxane block copolymers for textile finishing purposes. Here, the usage of the polyethersiloxane improves the finished goods and hydrophilicity.

US 2007/0286837, US 2007/0041929, US 2008/0292575 and CN 101198311 describe combinations between silicone quats having a siloxane chain length of greater than 200 D-units and a second silicone for hair conditioning purposes. One possible choice of the second silicone is the choice of silicone polyethers derived from ethylene oxide or propylene oxide or mixtures thereof. Specific structures are not given.

None of the above prior art disclosures describes a straight forward methodology for the preparation of low viscosity polyorganosiloxanes comprising quaternary ammonium groups. Low viscosity materials would make the incorporation of hydrophilicity improving substituents such as polyethers superfluous or redundant, thus reducing the system complexity.

SUMMARY OF THE INVENTION

The present invention provides for a low viscosity silicone (oligomerimeric or polymeric siloxane that is a homopolymer, copolymer or terpolymer) functionalized with quaternary ammonium groups and comprising one or more terminal ester groups as follows: a polyorganosiloxane compound comprising:
a) at least one polyorganosiloxane group,
b) at least one quaternary ammonium group,
c) at least one terminal ester group,
wherein the molar ratio of the quaternary ammonium groups b) and the terminal ester groups c) is less than 100:15 and additionally optionally further comprising:
d) at least one polyalkylene oxide group.

The present invention further provides for a method of preparing the compounds of the present invention comprising the reaction of
(i) at least one ditertiary diamine,
(ii) at least one amino-alkylating compound, comprising at least one diepoxide, and
(iii) at least one monofunctional organic acid,
wherein at least one compound among compounds (i) and (ii) comprises polyorganosiloxane structural units.

DETAILED DESCRIPTION OF THE INVENTION

The present invention provides for low viscosity polyorganosiloxanes comprising quaternary ammonium groups, their manufacture and the use of the materials.

Surprisingly, polyorganosiloxanes comprising quaternary ammonium groups possessing a low viscosity is accomplished by the preparation of polyorganosiloxane compounds comprising quaternary ammonium groups and terminal ester groups. That is, in accordance with the present invention polyorganosiloxane compounds are provided comprising:
a) polyorganosiloxane groups,
b) quaternary ammonium groups,
c) terminal ester groups,
wherein the molar ratio of the quaternary ammonium groups b) and the terminal ester groups c) is less than 100:15, preferably less than 100:20. In a preferred embodiment the polyorganosiloxane compounds according to the invention, further comprises:
d) polyalkylene oxide groups.

The polyorganosiloxane compounds according to the invention preferably are linear copolymer compounds that comprise the above functional groups a), b) and optionally d) in at least two repeating units, with at least part of the terminal groups being terminal ester groups that result from the use of monofunctional organic acids as chain stoppers (formally [(A-B)$_x$-A]-type product (wherein x>1 and A does not denote the group A defined in the claims)). However, depending on the stoichiometry of the reactants the polyorganosiloxane compounds according to the invention may also comprise compounds resulting from the reaction of a difunctional monomer with just one compound at each terminal thereof ([(A-B)$_x$-A]-type product (where x=1 and A does not denote the group A defined in the claims)).

In a preferred embodiment the polyalkylene oxide groups are of the general formula:

-A-E-A'- wherein A and A' each are independently from each other selected from a single bond or a divalent organic group having up to 10 carbon atoms and one or more hetero atoms, and E is a polyalkylene oxide group of the general formulae:

—[CH$_2$CH$_2$O]$_q$—[CH$_2$CH(CH$_3$)O]$_r$—[CH$_2$CH(C$_2$H$_5$)O]$_s$— with
q=0 to 200,
r=0 to 200,
s=0 to 200
and q+r+s=1 to 600.

In a preferred embodiment of the polyorganosiloxane compounds according to the invention the at least one polyorganosiloxane group are of the general formula:

—K—S—K—, with

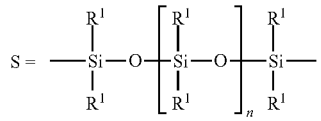

wherein $R^1$=C$_1$-C$_{22}$-alkyl, C$_1$-C$_{22}$-fluoroalkyl or aryl, n=0 to 1000, and these can be identical or different if several S Groups are present in the polyorganosiloxane compound, preferably for example n is for example in the range 0-200 or >200 to 1000;

K=is a bivalent or trivalent straight chain, cyclic and/or branched C$_2$-C$_{40}$ hydrocarbon residue which is optionally interrupted by —O—, —NH—, trivalent N, —NR$^1$—, —C(O)—, —C(S)—, and optionally substituted with —OH, wherein R$^1$ is defined as above, whereby the residues K can be identical or different from each other. In such group —K—S—K— the residue K is bound to the silicon atom of the residue S via a C—Si-bond.

In a preferred embodiment the polyorganosiloxane compounds according to the invention comprise at least one repeating unit comprising at least one quaternary ammonium group selected from the general formulas:

—N$^+$R$_2$—,

—N$^+$R$_2$-T-N$^+$R$_2$—, a saturated or unsaturated mono or diquaternary heterocycle of the formulae

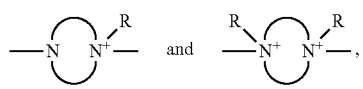  and and
an aromatic ammonium heterocycle of the formula

wherein R is selected from monovalent organic groups having up to 22 carbon atoms and optionally one or more heteroatoms, and wherein the free valencies at the nitrogen atoms are bound to carbon atoms, and T is selected from a divalent organic group having up to 20 carbon atoms and one or more hetero atoms in the present invention the term quaternary ammonium group relates to a positively charged nitrogen atom that binds to 4 carbon atoms (formally known as NR$^4$+ groups).

In a preferred embodiment the groups A and A' are selected from groups that result from the reaction of difunctional alkylating polyalkylene oxide compounds with di-tertiary amines (leading to quaternary ammonium groups) or with di-primary or secondary amines (leading to amine or ammonium groups). Such linking groups A and A' may include for example:

a single bond,
—CH$_2$CH(CH$_3$)—
—[CH$_2$CH$_2$O]$_q$—[CH$_2$CH(CH$_3$)O]$_r$—[CH$_2$CH(C$_2$H$_5$)O]$_s$—
—CH$_2$C(O)O—, —CH$_2$CH$_2$C(O)O—, —CH$_2$CH$_2$CH$_2$C(O)O—,
—OC(O)CH$_2$—, —OC(O)CH$_2$CH$_2$—, —OC(O)CH$_2$CH$_2$CH$_2$—,
—CH$_2$C(O)—, —CH$_2$CH$_2$C(O)—, —CH$_2$CH$_2$CH$_2$C(O)—,
—C(O)CH$_2$—, —C(O)CH$_2$CH$_2$—, —C(O)CH$_2$CH$_2$CH$_2$—,
—CH$_2$CH(OH)CH$_2$—, —O—CH$_2$CH(OH)CH$_2$—,
—CH$_2$CH(OH)CH$_2$—O—,
—[CH$_2$CH$_2$O]$_q$—[CH$_2$CH(CH$_3$)O]$_r$—[CH$_2$CH(C$_2$H$_5$)O]$_s$—

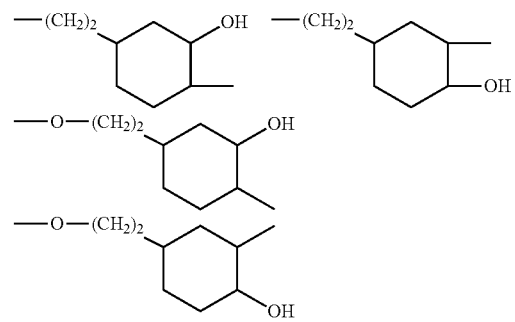

In a preferred embodiment of the invention the terminal ester groups are selected from the group of:
—OC(O)—Z
—OS(O)$_2$—Z
—OS(O$_2$)O—Z
—OP(O)(O—Z)OH
—OP(O)(O—Z)$_2$ wherein Z is selected from monovalent organic residues having up to 40 carbon atoms, optionally comprising one or more hetero atoms. As will be explained in detail below these terminal ester groups result from the use of monofunctional organic acids, like carboxylic acids (—OC(O)—Z), sulfonic acids (—OS(O)$_2$—Z), sulfuric acid half ester (—OS(O$_2$)O—Z), phosphoric acid mono ester (—OP(O)(O—Z)OH), phosphoric acid diester (—OP(O)(O—Z)$_2$) in the reaction with diepoxides.

In a preferred embodiment the polyorganosiloxane compounds according to the invention have the general formulas (Ia) and (Ib):

$$M\text{-}Y\text{—}[\text{—}(N^+R_2\text{-}T\text{-}N^+R_2)\text{—}Y\text{—}]_m\text{—}[\text{—}(NR^2\text{-}A\text{-}E\text{-}A'\text{-}NR^2)\text{—}Y\text{—}]_k\text{-}M \quad (Ia)$$

$$M\text{-}Y\text{—}[\text{—}(N^+R_2\text{-}T\text{-}N^+R_2)\text{—}Y\text{—}]_m\text{—}[(N^+R^2{}_2\text{-}A\text{-}E\text{-}A'\text{-}N^+R^2{}_2)\text{—}Y\text{—}]_k\text{-}M \quad (Ib)$$

wherein:

m is >0, preferred 0.01 to 100, more preferred 0.1 to 100, even more preferred 1 to 100, specifically 1 to 50, more specifically 1 to 20, even more specifically 1 to 10, k is 0 or an average value of >0 to 50 preferred 1 to 20, more preferred 1 to 10, M represents a terminal group, comprising terminal ester groups selected from

—OC(O)—Z
—OS(O)$_2$—Z
—OS(O$_2$)O—Z
—OP(O)(O—Z)OH
—OP(O)(O—Z)$_2$ wherein Z is as defined above,
-A-E-A'- is as defined above,
$R^2$ is selected from hydrogen or R,
Y is a group of the formula:

—K—S—K— and -A-E-A'- or -A'-E-A-, each as defined above, and
T is a as defined above.

Due to the possible presence of amine groups (—(NR$^2$-A-E-A-NR$^2$)—) in the polyorganosiloxane compounds according to the invention, they may have protonated ammonium groups, resulting from the protonation of such amine groups with organic or inorganic acids. Such compounds are sometimes referred to as acid addition salts of the polyorganosiloxane compounds according to the invention.

In a preferred embodiment the molar ratio of the quaternary ammonium groups b) and the terminal ester groups c) is less than 100:20, even more preferred is less than 100:30 and is most preferred less than 100:50. The ratio can be determined by $^{13}$C-NMR.

The polyorganosiloxane compounds according to the invention are manufactured preferably by a process, which comprises the reaction of
(i) at least one ditertiary diamine,
(ii) at least one amino-alkylating compound, comprising at least one diepoxide, and
(iii) at least one monofunctional organic acid,
wherein at least one compound among compounds (i) and (ii) comprises polyorganosiloxane structural units. In a further embodiment of this process in addition to the components (i) to (iii), component (iv), i.e. di-primary amine or di-secondary amines are reacted in such process.

In a preferred embodiment of the process according to the invention the at least one compound among compounds (i) and (ii) further comprise the polyalkylene oxide structural units as described before.

The present invention further relates to polyorganosiloxane compounds that are obtainable by the process according to the invention as described before.

A further embodiment of the present invention relates to polyorganosiloxane compositions, comprising:
A) at least one polyorganosiloxane compound, comprising
a) at least one polyorganosiloxane group,
b) at least one quaternary ammonium group,
c) at least one terminal ester group, and
d) optionally at least one polyalkylene oxide group (as defined before), B) at least one polyorganosiloxane compound, comprising at least one terminal ester group, different from compound A).

In the definition of component A) it can be referred to the description of the polyorganosiloxane compounds of the invention. The polyorganosiloxane compound B) differs from the polyorganosiloxane compound A) preferably in that it does not comprise quaternary ammonium groups. Preferred polyorganosiloxane compounds B) result from the reaction of monofunctional organic acids, in particular carboxylic acids, and polyorganosiloxane containing bisepoxides.

In the polyorganosiloxane compositions according to the invention the weight ratio of compound A) to compound B) is preferably less than 90:10. Or with other words, the content of component B) is at least 10 weight percent. In a further preferred embodiment of the polyorganosiloxane compositions according to the invention in compound A) the molar ratio of the quaternary ammonium groups b) and the terminal ester groups c) is less than 100:10, even more preferred is less than 100:15 and is most preferred less than 100:20.

Both, the polyorganosiloxane compounds or the polyorganosiloxane compositions according to the invention preferably have a viscosity at 20° C. and a shear rate of 0.1 s$^{-1}$ (plate-plate system, plate diameter 40 mm, gap width 0.5 mm) of less than 100000 mPa·s (100 Pa·s).

The present invention further relates to aqueous emulsions comprising at least one polyorganosiloxane compound and/or at least one polyorganosiloxane composition as defined above or below. Such aqueous emulsions preferably comprise at least 30 weight percent, preferably at least 50 weight percent, still more preferably at least 80 weight percent water based on the total weight of the emulsions.

The present invention further relates to a method of surface treatment, comprising the step of applying the polyorganosiloxane compounds, the polyorganosiloxane compositions or the aqueous emulsions thereof as defined in any of the previous claims, to the surface of a substrate. Any method of applying it is conceivable, e.g. simple wetting, contacting, washing, dipping, spraying, brushing, spreading operations conventionally known in the art can be referred to.

In such method preferably one of a following compositions or formulations respectively are applied: cosmetic formulations for skin and hair care, selected from Rinse-off and Leave-on conditioners, shampoos, styling gels, sprays, and pump sprays; formulations for polishing for the treatment and outfitting of hard surfaces; formulations for drying automobiles and other hard surfaces; formulations for initial outfitting of textiles and textile fibers; softener formulations comprising in addition non-ionogenic or anionic/non-ionogenic or cationic or betaine surfactants for application during or after washing textiles; laundry formulations for textile washes based upon non-ionic or anionic/non-ionic or cationic or betaine surfactants or formulations for preventing or reversing textile crumpling.

Further Preferred Embodiments Of The Invention:

In the polyalkylene oxide group E of the general formulae:

—[CH$_2$CH$_2$O]$_q$—[CH$_2$CH(CH$_3$)O]$_r$—[CH$_2$CH(C$_2$H$_5$)O]$_s$— the indices are preferably:
q=0 to 200, preferred 0 to 100, more preferred 0 to 50, still more preferred 0 to 20,
r=0 to 200, preferred 0 to 100, more preferred 0 to 50, still more preferred 0 to 20,
s=0 to 200, preferred 0 to 100, more preferred 0 to 50, still more preferred 0 to 20, and q+r+s=1 to 600, preferred 1 to 100, more preferred 1 to 50, even more preferred 1 to 40.

In the polyorganosiloxane structural unit with the general formula S:

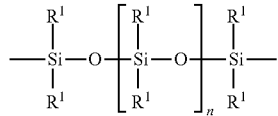

wherein $R^1=C_1-C_{22}$-alkyl, $C_1-C_{22}$-fluoralkyl or aryl, n=0 to 1000, preferred 0 to 500, more preferred 0 to 300, even more preferred 0 to 200, specifically 0 to 100 or in some instances >200 to 1000.

K (in the group —K—S—K—) is preferably a bivalent or trivalent straight chain, cyclical or branched $C_2-C_{20}$ hydrocarbon residue which is optionally interrupted by —O—, —NH—, trivalent N, —NR$^1$—, —C(O)—, —C(S)—, and optionally substituted with —OH.

In the polyorganosiloxanes of the invention the positive charges resulting from the ammonium group(s), are neutralized with inorganic anions such as chloride, bromide, hydrogen sulfate, sulfate, or organic anions, like carboxylates deriving from $C_1-C_{30}$ carboxylic acids, for example acetate, propionate, octanoate, especially from $C_{10}-C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be inter alia modified based upon the selection of acids used.

Quaternary ammonium groups as contained in the polyorganosiloxanes of the invention are usually generated by reacting the di-tertiary amines with an alkylating agents, selected from in particular di-epoxides (sometimes referred to also as bis-epoxides) in the presence of mono carboxylic acids and difunctional dihalogen alkyl compounds.

$R^1$ is more preferred $C_1-C_{18}$ alkyl, $C_1-C_{18}$ fluoroalkyl and aryl. Furthermore, $R^1$ is preferably $C_1-C_{18}$ alkyl, $C_1-C_6$ fluoroalkyl and aryl. Furthermore, $R^1$ is preferably $C_1-C_6$ alkyl, $C_1-C_6$ fluoroalkyl, more preferably $C_1-C_4$ fluoroalkyl, and phenyl. Even more preferably, $R^1$ is methyl, ethyl, trifluoropropyl and phenyl.

In the framework of the present invention, the term "$C_1-C_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl serve as examples.

In the framework of the present invention, the concept "$C_1-C_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are presented as examples.

In the framework of the present invention, "aryl" means unsubstituted or phenyl substituted once or several times with OH, F, Cl, CF$_3$, $C_1-C_6$ alkyl, $C_1-C_6$ alkoxy, $C_3-C_7$ cycloalkyl, $C_2-C_6$ alkenyl or phenyl. The expression can also mean naphthyl if need be.

In a preferred embodiment the polyorganosiloxane compounds are of the general formulas (Ia) and (Ib):

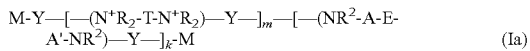

(Ia)

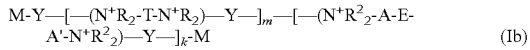

(Ib)

wherein each group is as defined above. In such formula the repeating units are usually in a statistical arrangement (i.e not a block-wise arrangement).

In a further preferred embodiment the polyorganosiloxane compounds may be also of the general formulas (IIa) or (IIb):

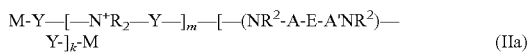

(IIa)

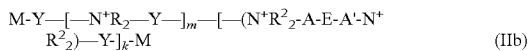

(IIb)

wherein each group is as defined above. Also in such formula the repeating units are usually in a statistical arrangement (i.e not a block-wise arrangement).

Z in the groups M:
—OC(O)—Z
—OS(O)$_2$—Z
—OS(O$_2$)O—Z
—OP(O)(O—Z)OH
—OP(O)(O—Z)$_2$

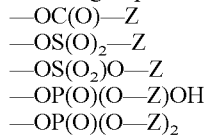

is preferably is a straight chain, cyclic or branched saturated or unsaturated $C_1-C_{20}$, preferred $C_2$ to $C_{18}$, even more preferred-hydrocarbon radical, which can be interrupted by one or more —O—, or —C(O)— and substituted with —OH.

Preferred groups M are —OC(O)—Z resulting from normal carboxylic acids in particular with more than 10 carbon atoms like for example dodecanoic acid.

In a preferred embodiment of the invention the molar ratio of the polyorganosiloxane-containing repeating group —K—S—K— and the polyalkylene repeating group -A-E-A'- or -A'-E-A- is between 100:1 and 1:100, preferred between 20:1 and 1:20, even more preferred between 10:1 and 1:10.

In the group —(N$^+$R$_2$-T-N$^+$R$_2$)— the groups R preferably represent a monovalent straight chain, cyclic or branched $C_1-C_{20}$ hydrocarbon radical, which can be interrupted by one or more —O—, —C(O)— and can be substituted by —OH, T preferably represent a divalent straight-chain, cyclic, or branched $C_1-C_{20}$ hydrocarbon radical, which can be interrupted by —O—, —C(O)— and can be substituted by hydroxyl.

The viscosities of the neat polymers according to this embodiment of the invention preferably are 500 to 100000 mPa·s, preferred 500 to 70000 mPa·s, more preferred 500 to 50000 mPa·s, even more preferred 500 to 20000 mPa·s, specifically 500 to 10000 mPa·s, more specifically 500 to 5.000 mPa·s determined at 20° C. and a shear rate of 0.1 s$^{-1}$. The molecular weight is between 10,000 and 100,000 g/mol measured as weight average Mw per GPC (gel permeation chromatography) and polystyrene as standard.

This molar ratio of the polyorganosiloxane-containing repeating group —K—S—K— and the polyalkylene repeating group -A-E-A'- or -A'-E-A- can be controlled as shown below via the selection of the molar ratio of the parent compounds, especially the ratio of the α,ω-halogen alkyl carboxylic acid polyalkylene oxide ester compounds preferably used in the invention and the polyorganosiloxane-bis epoxide compounds. The properties of the products depend essentially upon the ratio of the parent materials used, and upon the length of the polyalkylene oxide or polyorganosiloxane blocks contained therein.

In a preferred embodiment of the invention, K is a divalent hydrocarbon radical having at least 4 carbon atoms, which contains one hydroxy group and can be interrupted by one oxygen atom. Such groups include for example:

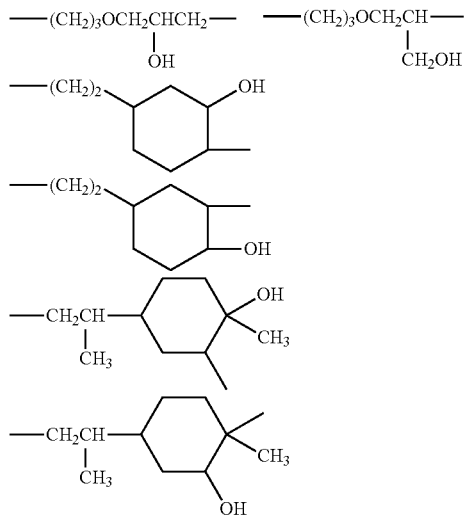

In the groups

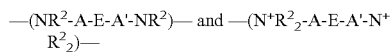

preferably, the group -A-E-A'- is represented by a group of the formula

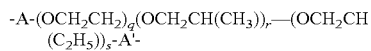

wherein A is a single bond or a straight chain or branched $C_1$-$C_6$ alkanediyl group with q preferably 0 to 100, more preferably 0 to 70, even more preferably 0 to 40, r preferably 0 to 100, more preferably 0 to 70, even more preferably 0 to 40, s preferably 0 to 100, more preferably 0 to 70, even more preferably 0 to 40, q+r+s=1 to 300, more preferably 1 to 100, even more preferred 1 to 50, In the group -A-($OCH_2CH_2$)$_q$—($OCH_2CH(CH_3)$)$_r$—($OCH_2CH(C_2H_5)$)$_s$-A'- the ethylene oxide and propylene oxide and butylenes oxide units can be positioned in any way, e.g. as statistical copolymer units or as a block copolymer unit.

The polyorganosiloxane compounds of the invention are preferentially produced in a first embodiment via a method, in which first α,ω Si—H functionalized siloxanes of the general structure

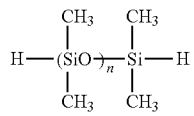

are converted, in the presence of a hydrosilylation catalyst and at temperatures of 50° to 150° C., with 1.0 to 1.5 mol, based upon SiH groups, of an alkenyl-epoxide, which has a terminal olefinic bond, wherein the alkenyl-epoxide contains at least 4 carbon atoms, and may additionally contain a non-cyclical ether group. Vinyl cyclohexene oxide and allylglycide ether are preferably used as epoxy-functional precursors for the production of epoxy functionalized siloxanes. The excess olefinic epoxide is then removed, if necessary.

The bisepoxide is preferably reacted with a mixture of one diamine, for example the preferred diamine of the formula

with R and T as defined above, and one α,ω carboxylic halogen alkyl acid ester, preferably of the formula

wherein A-E-A' or A'-E-A are as defined above and X is a customary nucleophilic originating group, preferably chloride or bromide, provided that X is bonded to a terminal —$CH_2$-group, in the presence of an organic acid at preferred 40° to 150° C., wherein the molar ratio of tertiary amino groups: carboxylic haloacid ester groups is for example ≥1:1, the molar ratio of tertiary amino groups: Σ(epoxy groups+carboxylic haloacid ester groups) is for example ≤1:1, preferred ≤0.98:1, more preferred ≤0.9:1, even more preferred ≤0.7:1, specifically ≤0.5:1, the molar ratio of organic acid: epoxy groups ranges from 3:1 to 1:1, preferred from 2:1 to 1:1, more preferred from 1.5:1 to 1:1, even more preferred from 1.2:1 to 1:1, specifically is 1:1.

This means that i.e. either by reduction of the molar amount on tertiary amine and/or increase of the molar amount of organic acids low viscosity polyorganosiloxane compounds of the invention can be synthesized.

In a preferred variation of the embodiment, the species that contain the various amino groups may be added to the batch together with the carboxylic haloacid ester derivatives, if necessary with the simultaneous addition of equimolar quantities of acid. It is also within the scope of the invention, however, to cause first the epoxy derivatives, the carboxylic haloacid ester derivatives, and the di-tertiary amines to react in the presence of a quantity of acid that is equivalent to that of the epoxy groups, and then, if necessary, to add alkylene oxide derivatives that contain primary or secondary amino groups, if necessary with the addition of acids to the point of equivalence with the amino groups.

It is likewise possible to bring the carboxylic haloacid ester derivatives and the di-tertiary amines to react, forming hydrophilic blocks, and afterwards to add the epoxy derivatives, if necessary adding alkylene oxide derivatives that contain primary or secondary amino groups, in the presence of a quantity of acid that is equivalent to that of the epoxy groups to the reaction mixture.

It is preferred to use bis carboxylic haloacid esters of polyalkylenoxides such as alpha, omega bis-chloroacetic esters of polyethylene oxides, alpha, omega diamino terminated polyalkylene oxides (Jefamine®) and alpha, omega diepoxy terminated polyalkylene oxides such as DER®, e.g. 632 or 636, as precursors for the polyalkylene oxide moiety in the siloxane copolymers.

During the time in which the individual components are being added, the sequential distribution in the polymers being formed can be influenced.

It is further within the scope of the invention to cause several siloxane components and/or alkylene oxide derivatives of various chain lengths to react, while maintaining the desired overall stoichiometry. From this, there follows, e.g., the possibility of creating a desired siloxane chain length by using a single siloxane component or by the purposeful mixture of several siloxane components. Analogously, it is possible to prepare an advantageous average alkylene oxide block length in the form of a monomodal, bimodal, or polymodal dispersion. Further, a desired share of alkylene oxides can be distributed variably between the carboxylic haloacid ester components and the amino components.

Parent materials for the production of the preferred α,ω carboxylic haloacid esters, preferably of the formula X-A-E-A'-X or X-A-E-A'-X wherein X is preferably chlorine, bromine, are expediently low-molecular, oligomeric and polymeric alkylene oxides of the general composition $H(OCH_2CH_2)_q(OCH_2CH(CH_3))_r$—$(OCH_2CH(C_2H_5))_s OH$ wherein q, r and s have the meanings indicated above. Preferred representatives are diethylene glycol, triethylene glycol, tetraethylene glycol, the oligoethylene glycols having molar weights of 300 to 1,000 g/mol, especially approximately 400, approximately 600, and approximately 800, dipropylene glycol, tripropylene glycol, tetraproylene glycol, polypropylene glycols having molar weights of 300 to 3,000 g/mol, especially approximately 300, approximately 600 and approximately 2000 and poly(ethylene-propylene)glycol copolymers having molar weights of 300 to 3,000 g/mol. The esterification is accomplished via known methods. For descriptions of said methods please refer to WO 02/10257, example 11a.

Preferred alkylene oxide derivatives used in accordance with the invention are commercially available under the name Jeffamine® (Huntsman Corp.).

The quaternization and alkylation reactions are preferably run in polar organic solvents.

Suitable solvents are, for example organic solvents and water, including in particular mixtures of organic solvents and water, preferably polar organic solvents and water. Polar organic solvents include generally those comprising at least one heteroatome, like in particular oxygen, e.g., alcohols, especially methanol, ethanol, i-propanol and n-butanol; glycols, such as ethylene glycol, diethylene glycol, triethylene glycol, their methyl-, ethyl- and butyl ethers, 1,2-propylene glycol, dipropylene glycol, tripropylene glycol, their methyl-, ethyl- and butyl ethers and 1,3-propylene glycol; ketones, such as acetone and methylethylketone; esters, such as ethylacetate, butylacetate, methoxypropylacetate and 2-ethylhexylacetate; ethers, such as tetrahydrofuran; and nitro compounds, such as nitromethane.

It is preferred to run the reactions with a weight ratio of Σ polymer components: Σ(organic solvents+water) in a weight-range from 100:0 to 20:80, preferably 99.999:0.001 to 20:80, more preferred 95:5 to 20:80, still more preferred 95:5 to 50:50, even more preferred 95:5 to 60:40.

The amount on water in the composition of the reaction ranges in one embodiment from 0.1-0.5 wt. % wt. %, in another one preferably from 0.01-0.1; in an other embodiment the amount is in the range of 2-10 wt. % and preferably between 0.5-2 wt. %. In a preferred embodiment of the invention the desired amount on water is added separately. It is also possible to add the desired amount on water i.e. in form of solvent azeotropes or by the amount which is present in commercial grades.

The above described polyorganosiloxane compounds comprising quaternary ammonium functions and ester functions may contain individual molecules which contain quaternary ammonium functions and no ester functions, molecules which contain quaternary ammonium functions and ester functions as well as molecules which contain ester functions and no quaternary ammonium functions.

The above described polyorganosiloxane compounds comprising quaternary ammonium functions and ester functions are to be understood as mixtures of molecules comprising a certain averaged amount and ratio of both moieties.

Another less preferred embodiment of the invention relates to polyorganosiloxane compositions, comprising:
A) at least one polyorganosiloxane compound, comprising
  a) at least one polyorganosiloxane group,
  b) at least one quaternary ammonium group,
  c) at least one terminal ester group, and
B) at least one polyorganosiloxane compound, comprising at least one terminal ester group, different from compound A).

Such polyorganosiloxane compositions comprising quaternary ammonium functions and polyorganosiloxane compounds comprising ester functions are physically mixed in order to adjust the desired quat (N$^+$): ester ratio and the desired viscosity according to the invention. Both compounds are mixed in a ratio which fulfils the above outlined viscosity requirement according to the invention. The mixtures have a viscosities at 20° C. and a shear rate of 0.1 s$^{-1}$ of <100000 mPas, preferred <50000 mPas, even more preferred <20000 mPas, specifically <10000 mPas, more specifically <5000 mPa·s. The polyorganosiloxane compounds A) comprising quaternary ammonium functions are i.e. known from WO 02/10257. The synthesis of polyorganosiloxane compounds comprising ester functions is known from WO 2011/064255. They can i.e. be synthesized from the corresponding epoxy siloxanes by esterification with acids in the presence of a tertiary amine catalyst. The preferred polyorganosiloxane compounds B) comprising ester functions are α,ω-ester modified derivatives of the structure M-(K—S$_n$—K)-M having siloxane chain length' in range from n=0 to 1000, preferred 0 to 500, more preferred 0 to 300, even more preferred 0 to 200, specifically 0 to 100. Alternatively, comb like derivatives comprising ester function as side groups in a difunctional siloxane unit (OSiMeR* with R*=carbon bound ester group)), and optionally terminal ester moieties (O$_{1/2}$SiMe$_2$R* with R*=carbon bound ester group) of the same chain length range of n are also preferred. The number of ester-group-containing siloxy units is preferably from 1 to 500, preferred 1 to 250, more preferred 1 to 150, even more preferred 1 to 100, specifically 1 to 50, even more specific 1 to 25.

Preferred monofunctional organic acids yielding the esters are the ones forming the above mentioned counter ions. Preferred examples are $C_1$-$C_{30}$ carboxylic acids, for example C2, C3, C8 acids, $C_{10}$-$C_{18}$ carboxylic acids, for example C12, C14, C16 acids, saturated, unsaturated and hydroxyl functionalized C18 acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

The invention further relates to the use of the above-described polyorganosiloxane compounds in cosmetic formulations for skin and hair care, in polishing agents for treating and coating hard surfaces, in formulations for drying automobiles and other hard surfaces, for example following automatic washing, for finishing textiles and textile fibers, as separate softeners for use after textiles have been washed with non-ionogenic or anionic/non-ionogenic detergent formulations, as softeners in formulations for washing textiles that are based upon non-ionic or anionic/non-ionic surfactants, and as means for preventing or removing wrinkles in textiles.

The invention further relates to the use of the above-described polyorganosiloxane compounds as wash-resistant, hydrophilic softeners for use in the original finishing of textiles.

The invention further relates to compositions that contain at least one of the polyorganosiloxane compounds, together with at least one additional component that is commonly used in such a composition.

Below, a number of typical examples of these types of compositions are provided, in which the polyorganosiloxane compounds of the invention may be advantageously used:

Typical adjuvants in these types of compositions are, e.g., those materials described in A. Domsch: Die kosmetischen Praeparate [Cosmetic Preparations] Vol. I and II, 4$^{th}$ Edition, Verl. fuer chem. Industrie [Publishers for the Chemical Industry], U. Ziolkowsky K G, Augsburg, and the International Cosmetic Ingredient Dictionary and Handbook 7$^{th}$ Ed. 1997 by J. A. Wenninger, G. N. McEwen Vol. 1-4 by The Cosmetic, Toiletry and Fragrance Association Washington D.C.

Anionic Shampoo

This formulation example is intended as a basic formulation. Anionic shampoos customarily contain, but are not limited to, the following components:

Alkylsulfates, alkylether sulfates, sodium lauryl sulfate, sodium lauryl ether sulfate, ammonium lauryl sulfate, ammonium lauryl-ether sulfate, TEA-lauryl sulfate, TEA-lauryl-ether sulfate, alkylbenzene sulfonates, α-olefinsulfonates, paraffin sulfonates, sulfosuccinates, N-acyltaurides, sulfate-glycerides, sulfatized alkanolamides, carboxylate salts, N-acyl-amino acid salts, silicones, etc.

| Components | wt-% |
| --- | --- |
| Ammonium lauryl sulphate | 10.00-30.00 |
| Ammonium lauryl-ether sulphate | 5.00-20.00 |
| Cocamidopropyl betaine | 0.00-15.00 |
| Lauramide DEA | 0.00-5.00 |
| Cocamide Mea | 0.00-5.00 |
| Dimethicone copolyol (dimethylsiloxane glycol copolymer) | 0.00-5.00 |
| Cyclopentasiloxane | 0.00-5.00 |
| Polyorganosiloxane compound of the invention | 0.50-5.00 |
| Polyquaternium-10 | 0.00-2.00 |
| Preservatives | 0.00-0.50 |
| Fragrance | 0.00-5.00 |
| Deionized water | q.s. 100% |
| Sodium chloride | q.s. |

Non-Ionic Shampoo

This formulation example is intended as a basic formulation. Non-ionic shampoos customarily contain, but are not limited to, the following components:

Monoalkanolamides, monoethanolamides, monoisopropanolamides, polyhydroxy derivatives, sucrose monolaurate, polyglycerine ether, amine oxides, polyethoxylated derivatives, sorbitol derivatives, silicones, etc.

| Components | Wt-% |
| --- | --- |
| Lauramide DEA | 10.00-30.00 |
| Lauramide oxide | 5.00-20.00 |
| Cocamide Mea | 0.00-5.00 |
| Dimethicone copolyol | 0.00-5.00 |
| Polyorganosiloxane compound of the invention | 0.50-5.00 |
| Preservatives | 0.00-0.50 |
| Fragrance | 0.00-5.00 |
| Deionized water | q.s. 100% |
| Sodium chloride | q.s. |

Amphoteric Shampoo

This formulation example is intended as a basic formulation. Formulations of this category customarily contain, but are not limited to, the following components:

N-alkyl-iminodipropionates, N-alkyl-iminopropionates, amino acids, amino acid derivatives, amido betaine, imidazolinium derivatives, sulfobetaines, sultaines, betaines, silicones, etc.

| Components | Wt-% |
| --- | --- |
| PEG-80-sorbitane laurate | 10.00-30.00 |
| Lauroamphoglycinate | 0.00-10.00 |
| Cocamidopropyl-hydroxysultain | 0.00-15.00 |
| PEG-150-distearate | 0.00-5.00 |
| Laurylether-13-carboxylate | 0.00-5.00 |
| Polyorganosiloxane compound of the invention | 0.50-5.00 |
| Fragrance | 0.00-5.00 |
| Deionized water | q.s. 100% |
| Sodium chloride | q.s. |

Cationic Shampoo

This formulation example is intended only as a basic formulation. Formulations of this category customarily contain, but are not limited to, the following components:

Bis-quaternary ammonium compounds, bis-(trialkylammonium acetyl)diamines, amido amines, ammonium alkylesters, silicones, etc.

| Components | Wt-% |
| --- | --- |
| Laurylether-13-carboxylate | 10.00-30.00 |
| Isopropylmyristate | 5.00-20.00 |
| Cocamidopropyl-betaine | 0.00-15.00 |
| Lauramide DEA | 0.00-5.00 |
| Cocamide MEA | 0.00-5.00 |
| Polyorganosiloxane compound specified in the invention | 0.50-5.00 |
| Preservatives | 0.00-0.50 |
| Fragrance | 0.00-5.00 |
| Deionized water | q.s. 100% |
| Sodium chloride | q.s. |

Setting Agents

This formulation example is intended only as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickeners, silicones, etc.

| Components | Wt-% |
| --- | --- |
| Ceteareth-20 | 0.10-10.00 |
| Steareth-20 | 0.10-10.00 |
| Stearyl alcohol | 0.10-10.00 |
| Stearamidopropyl-dimethylamine | 0.00-10.00 |
| Dicetyldimonium-chloride | 0.00-10.00 |
| Polyorganosiloxane compound of the invention | 0.50-5.00 |
| Cyclopentasiloxane | 0.00-5.00 |
| Dimethicone | 0.00-5.00 |
| Preservatives | 0.00-0.50 |
| Fragrance | 0.00-5.00 |
| Deionized water | q.s. 100% |

"Clear Rinse-Off" Setting Agents

This formulation example is intended as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, etc.

| Components | Wt-% |
| --- | --- |
| Glycerin | 0.10-10.00 |
| Cetrimonium chloride | 0.00-10.00 |
| Polyorganosiloxane compound of the invention | 0.50-5.00 |
| Hydroxyethyl cellulose | 0.00-5.00 |
| Preservatives | 0.00-0.50 |
| Fragrance | 0.00-5.00 |
| Deionized water | q.s. 100% |

Foam Setting Agents for Hair

This formulation example is intended as a basic formulation. Formulations of this category contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
| --- | --- |
| Polyorganosiloxane compound of the invention | 0.50-5.00 |
| Nonoxynol-15 | 0.00-2.00 |
| Nonoxynol-20 | 0.00-2.00 |
| Fragrance | 0.00-5.00 |
| Aerosol propellants | 0.00-20.00 |
| Preservatives | 0.00-0.50 |
| Deionized water | q.s. 100% |

Pump Spray (Setting Agents) for Hair

This formulation example is intended only as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, etc.

| Components | Wt-% |
| --- | --- |
| Polyorganosiloxane compound of the invention | 0.50-5.00 |
| Cyclomethicone | 0.00-80.00 |
| Ethanol | 0.00-80.00 |
| Preservatives | 0.00-0.50 |
| Fragrance | 0.00-5.00 |
| Deionized water | q.s. 100% |

Setting Agent Spray for Hair

This formulation example is intended as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
| --- | --- |
| Polyorganosiloxane compound of the invention | 0.50-5.00 |
| Cyclomethicone | 0.00-80.00 |
| Ethanol | 0.00-50.00 |
| Aerosol propellants | 0.00-50.00 |
| Preservatives | 0.00-0.50 |
| Fragrance | 0.00-5.00 |
| Deionized water | q.s. 100% |

Gel Setting Agents for Hair

This formulation example is intended as a basic formulation. Formulations of this category customarily contain, but are not limited to, the following components: thickening agents, cellulose derivatives, acrylic acid derivatives, fixative polymers, conditioning chemicals, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, silicones, solvents, ethanol, isopropanol, isoparaffin solvents, etc.

| Components | Wt-% |
| --- | --- |
| Polyorganosiloxane compound of the invention | 0.50-5.00 |
| Hydroxyethyl cellulose | 0.00-2.00 |
| Fragrance | 0.00-5.00 |
| Preservatives | 0.00-0.50 |
| Citric acid | 0.00-2.00 |
| Deionized water | q.s. 100% |

Rinse Off Conditioner

This formulation example is intended as a basic formulation. Formulations of this category customarily contain, but are not limited to, the following components: hydrocarbon based cationic conditioning agents, silicone based cationic conditioning agents, high melting fatty compounds, low melting oil like ester compounds, thickening agents, cellulose derivatives, fixative polymers, ethylene glycols, propylene glycols, glycol esters, glycerin, glycerin esters, monohydric alcohols, polyhydric alcohols, cationic polymers, nonionic and betain co-emulsifiers, silicones, complexing agents, solvents, fragrances, vitamins, solvents, etc.

| Components | Wt-% |
| --- | --- |
| Polyorganosiloxane compound of the invention | 0.50-10.00 |
| Cetyl Hydroxyethyl cellulose | 0.00-3.00 |
| Cetearyl alcohol | 0.00-3.00 |
| Glyceryl stearate and PEG-100 Stearate | 0.00-3.00 |
| Tetrasodium EDTA | 0.00-1.00 |
| Deionized water | q.s. 100% |

Styling Gel for Hair

This formulation example is intended as a basic formulation. Formulations of this category customarily contain, but are not limited to, the following components:

Fixative polymers, lacquers, acrylic acid derivatives, cellulose derivatives, vinyl derivatives, conditioning chemicals, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, etc.

| Components | % |
| --- | --- |
| Polyorganosiloxane compound of the invention | 0.50-5.00 |
| Fixing agents | 0.10-10.00 |
| Hydroxyethyl cellulose | 0.00-2.00 |
| Fragrance | 0.00-5.00 |
| Citric acid | 0.00-2.00 |
| Deionized water | q.s. 100% |

Styling Spray for Hair

This formulation example is intended as a basic formulation. Formulations of this category customarily contain, but are not limited to, the following components:

Fixative polymers, lacquers, vinyl derivatives, fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
| --- | --- |
| Polyorganosiloxane compound of the invention | 0.50-5.00 |
| Cyclomethicone | 0.00-80.00 |
| Fixing agents | 0.10-10.00 |
| Ethanol | 0.00-50.00 |
| Aerosol propellants | 0.00-50.00 |
| Preservatives | 0.00-0.50 |
| Fragrance | 0.00-5.00 |
| Deionized water | q.s. 100% |

Pump Spray (Styling) for Hair

This formulation example is intended as a basic formulation. Formulations of this category customarily contain, but are not limited to, the following components:

Vinyl derivatives, fixative polymers, lacquers, fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
| --- | --- |
| Polyorganosiloxane compound of the invention | 0.50-5.00 |
| Fixing agents | 0.10-10.00 |
| Cyclomethicone | 0.00-80.00 |
| Ethanol | 0.00-50.00 |
| Preservatives | 0.00-0.50 |
| Fragrance | 0.00-5.00 |
| Deionized water | q.s. 100% |

The use of the polyorganosiloxane derivatives specified in the invention for applications in the hair care field produces favorable results with respect to strengthening, shine, fixing (hold), body, volume, moisture regulation, color retention, protection against environmental factors (UV, salt water, etc.), manageability, antistatic properties, ability to dye, etc.

EXAMPLES

The following examples are intended to describe the present invention in greater detail, without limiting its scope.

Example 1 (Non Inventive Polyorganosiloxane)

In a 500 ml three-necked flask, equipped with refluxing condenser, thermometer and mechanical stirrer, 150 g (58.7 mmol epoxy groups) of a silicone diepoxide of the structure

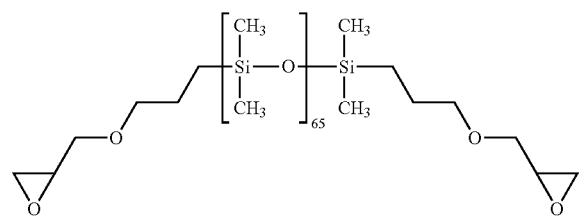

0.91 g (7 mmol $CH_2Cl$) $ClCH_2C(O)OCH_2CH_2OCH_2CH_2OC(O)CH_2Cl$, 12.56 g (62.8 mmol) lauric acid, 6.06 g N,N,N',N'-tetramethylhexanediamine (70.3 mmol tert. amine), 31.8 g 2-propanol and 10.7 g distilled water are mixed at room temperature. The mixture is heated to reflux for 13.5 hours. Afterwards, the solvents are removed and the material analyzed by means of NMR and viscometry (see tab. 1).

Example 2 (Inventive Polyorganosiloxane)

In a 500 ml three-necked flask, equipped with refluxing condenser, thermometer and mechanical stirrer, 150 g (58.7 mmol epoxy groups) of a silicone diepoxide of the structure

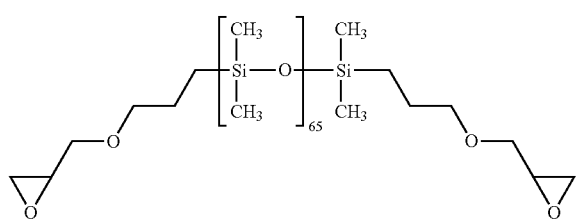

0.91 g (7 mmol CH$_2$Cl) ClCH$_2$C(O)OCH$_2$CH$_2$OCH$_2$CH$_2$OC(O)CH$_2$Cl, 12.56 g (62.8 mmol) lauric acid, 4.54 g N,N,N',N'-tetramethylhexanediamine (52.8 mmol tert. amine), 31.5 g 2-propanol and 10.5 g distilled water are mixed at room temperature. The mixture is heated to reflux for 13.5 hours. Afterwards, the solvents are removed and the material analyzed by means of NMR and viscometry (see tab. 1).

Example 3 (Inventive Polyorganosiloxane)

In a 500 ml three-necked flask, equipped with refluxing condenser, thermometer and mechanical stirrer, 150 g (58.7 mmol epoxy groups) of a silicone diepoxide of the structure

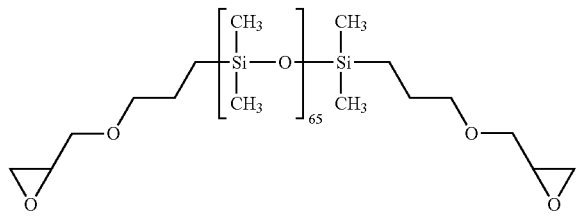

0.91 g (7 mmol CH$_2$Cl) ClCH$_2$C(O)OCH$_2$CH$_2$OCH$_2$CH$_2$OC(O)CH$_2$Cl, 12.56 g (62.8 mmol) lauric acid, 3.03 g N,N,N', N'-tetramethylhexanediamine (35.2 mmol tert. amino groups), 31.2 g 2-propanol and 10.4 g distilled water are mixed at room temperature. The mixture is heated to reflux for 13.5 hours. Afterwards, the solvents are removed and the material analyzed by means of NMR and viscometry (see tab. 1).

Example 4 (Inventive Polyorganosiloxane)

In a 500 ml three-necked flask, equipped with refluxing condenser, thermometer and mechanical stirrer, 150 g (58.7 mmol epoxy groups) of a silicone diepoxide of the structure

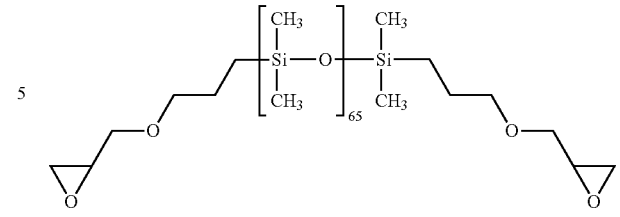

0.91 g (7 mmol CH$_2$Cl) ClCH$_2$C(O)OCH$_2$CH$_2$OCH$_2$CH$_2$OC(O)CH$_2$Cl, 12.56 g (62.8 mmol) lauric acid, 1.51 g N,N,N',N'-tetramethylhexanediamine (17.6 mmol tert. amino groups), 30.9 g 2-propanol and 10.3 g distilled water are mixed at room temperature. The mixture is heated to reflux for 13.5 hours. Afterwards, the solvents are removed and the material analyzed by means of NMR and viscosimetry (see tab. 1).

TABLE 1

| expl. # | solids % 120° C./30 min | viscosity mPa·s 20° C., 0.1 s$^{-1}$ | ratio N$^+$:ester ** | dispersibility in water* |
|---|---|---|---|---|
| 1 | 98.1 | 108,000 | 100:13.6 | very poor |
| 2 | 98.3 | 47,500 | 100:27.2 | acceptable |
| 3 | 98.3 | 9,100 | 100:49.8 | good |
| 4 | 97.7 | 700 | 100:55.8 | good |

*4 g of polyorganosiloxane material were added to 200 g of water and subjected to mixing with an Ultra Thurrax.
** ($^{13}$C-NMR)

The data show that example 1 yields a material which contains some ester functions but is too high in viscosity. As a consequence a very poor, uneven, lumpy and sticky dispersion in water is formed. Examples 2 to 4 show that reaction protocols according to the invention yield low viscosity materials which can be dispersed easily to small droplets having a sufficient stability.

Example 5 (Inventive Polyorganosiloxane Composition)

The product of example 1 is mixed with a lauroyl ester modified siloxane of the structure

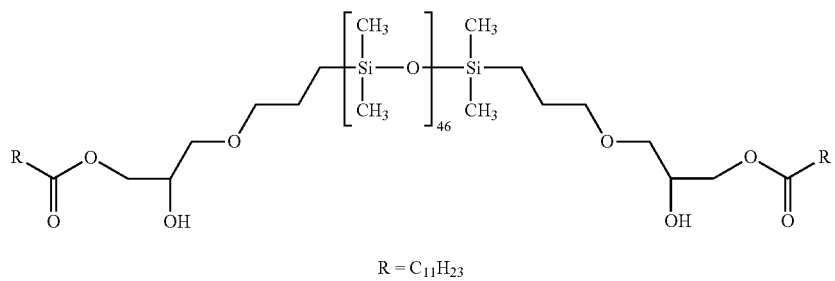

R = C$_{11}$H$_{23}$ which was synthesized from the corresponding epoxysiloxane, lauric acid and triethylamine (catalyst) in propylene glycol monomethyl ether according to WO 2011/064255.

The blending experiments are summarized in tab. 2.

TABLE 2

| expl. # | Weight ratio example 1:lauryl ester | viscosity mPa·s 20° C., 0.1 s$^{-1}$ | dispersibility in water* |
|---|---|---|---|
| 5.1 | 100:0 | 108,000 | very poor |
| 5.2 | 90:10 | 43,900 | acceptable |
| 5.3 | 75:25 | 17,000 | good |

TABLE 2-continued

| expl. # | Weight ratio example 1:lauryl ester | viscosity mPa·s 20° C., 0.1 s⁻¹ | dispersibility in water* |
|---|---|---|---|
| 5.4 | 50:50 | 3,100 | good |
| 5.5 | 25:75 | 830 | good |
| 5.6 | 0:100 | 270 | poor |

*4 g of polyorganosiloxane material were added to 200 g of water and subjected to mixing with an Ultra Thurrax.

The data for the examples 5.2 to 5.5 in tab.2 show that the physical blending of the non inventive material of example 1 with an ester modified siloxane yields mixtures which can be dispersed in water.

Example 6 (Starting Material)

In a 250 ml three-necked flask, equipped with refluxing condenser, thermometer and mechanical stirrer, 22.83 g allyl glycidyl ether (200 mmol epoxy groups) and 63.3 g (200 mmol amino groups) of an amine of the structure

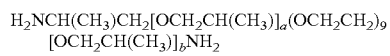
H$_2$NCH(CH$_3$)CH$_2$[OCH$_2$CH(CH$_3$)]$_a$(OCH$_2$CH$_2$)$_9$ [OCH$_2$CH(CH$_3$)]$_b$NH$_2$ with a+b=3.6

(Jeffamine ED 600, Huntsman) are mixed at room temperature. The mixture is heated to 120° C. for 90 minutes. Afterwards, volatiles are removed at 120° C./20 mbar over 30 minutes. A slightly brownish liquid of the structure

H(R)NCH(CH$_3$)CH$_2$[OCH$_2$CH(CH$_3$)]$_a$(OCH$_2$CH$_2$)$_9$ [OCH$_2$CH(CH$_3$)]$_b$N(R)H with R=—CH$_2$CH(OH)CH$_2$OCH$_2$CH=CH$_2$
is obtained. Solids content at 160° C./15 min 98.0%

Example 7 (Inventive Polyorganosiloxane)

In a 500 ml three-necked flask, equipped with refluxing condenser, thermometer and mechanical stirrer, 132.8 g (52 mmol epoxy groups) of a silicone diepoxide of the structure

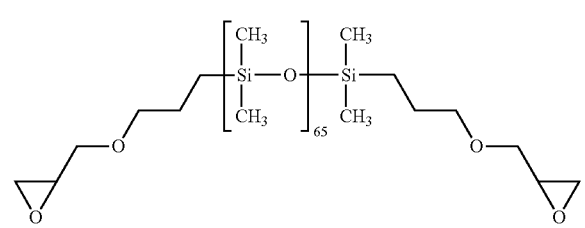

10.4 g (52 mmol) lauric acid, 3.22 g (37.4 mmol tert. amine) N,N,N',N'-tetramethylhexanediamine), 4.48 g (10.4 mmol sec. amino groups) of the starting material from example 6, 18.7 g propylene glycol mono methyl ether and 8.9 g distilled water are mixed at room temperature. The mixture is heated to reflux for 6 hours. Afterwards, the solvents are removed and the material analyzed by means of NMR and viscometry (see tab. 3).

Example 8 (Inventive Polyorganosiloxane)

In a 500 ml three-necked flask, equipped with refluxing condenser, thermometer and mechanical stirrer, 132.8 g (52 mmol epoxy groups) of a silicone diepoxide of the structure

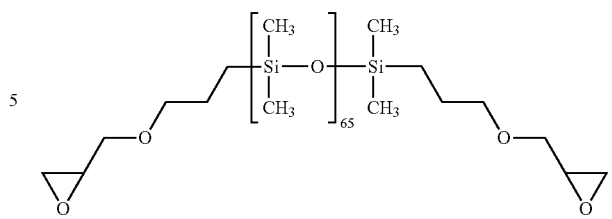

10.4 g (52 mmol) lauric acid, 1.24 g (15.6 mmol tert. amine) N,N,N',N'-tetramethylhexanediamine, 4.48 g (10.4 mmol sec. amino groups) of the starting material from example 6, 17.6 g propylene glycol mono methyl ether and 8.8 g distilled water are mixed at room temperature. The mixture is heated to reflux for 6 hours. Afterwards, the solvents are removed and the material analyzed by means of NMR and viscometry (see tab. 3).

TABLE 3

| Example | solids % 120° C./30 min | viscosity mPas 20° C., 0.1 s−1 | ratio N⁺:ester ** | dispersibility in water* |
|---|---|---|---|---|
| 7 | 97.4 | 15,000 | 100:31.4 | good |
| 8 | 97.8 | 1,500 | 100:98.8 | very good |

*4 g of polyorganosiloxane material were added to 200 g of water and subjected to mixing with an Ultra Thurrax.
** ($^{13}$C-NMR)

The examples show that polyorganosiloxanes according to the invention yield low viscosity materials which can be dispersed in water easily to small droplets having a sufficient stability.

Example 9 (Inventive Polyorganosiloxane)

In a 500 ml three-necked flask, equipped with refluxing condenser, thermometer and mechanical stirrer, 300 g (23.46 mmol epoxy groups) of a silicone diepoxide of the structure

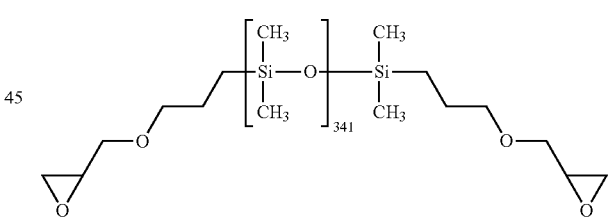

0.36 g (2.8 mmol CH$_2$Cl) ClCH$_2$C(O)OCH$_2$CH$_2$OCH$_2$CH$_2$C(O)CH$_2$Cl, 5.02 g (25.1 mmol) lauric acid, 1.21 g N,N,N',N'-tetramethylhexanediamine (14.05 mmol tert. amino groups), 57.7 g 2-propanol and 19.24 g distilled water are mixed at room temperature. The mixture is heated to reflux for 13.5 hours. During the reaction, after 2 hrs, 1 g triethylamine is added. Afterwards, the solvents are removed and the material analyzed by means solids and viscometry.
Solids % (120° C./30 min): 97.24
Viscosity mPa·s (20° C. 0.1 s⁻¹): 10.600

Example 10 (Inventive Polyorganosiloxane)

In a 500 ml three-necked flask, equipped with refluxing condenser, thermometer and mechanical stirrer, 300 g (23.46 mmol epoxy groups) of a silicone diepoxide of the structure

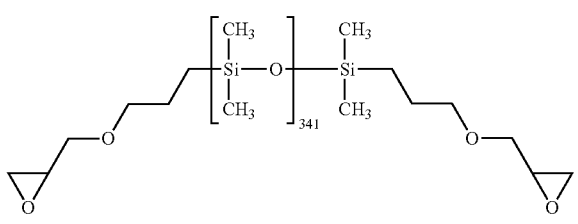

0.36 g (2.8 mmol CH$_2$Cl) ClCH$_2$C(O)OCH$_2$CH$_2$OCH$_2$CH$_2$OC(O)CH$_2$Cl, 5.02 g (25.1 mmol) lauric acid, 0.605 g N,N,N',N'-tetramethylhexanediamine (7.02 mmol tert. amino groups), 57.5 g 2-propanol and 18.88 g distilled water are mixed at room temperature. The mixture is heated to reflux for 13.5 hours. During the reaction, after 2 hrs, 1 g triethylamine is added. Afterwards, the solvents are removed and the material analyzed by means of solids and viscometry.

Solids % (120° C./30 min): 96.62
Viscosity mPas (20 OC 0.1 s$^{-1}$): 3500

The examples 9 to 10 show that low viscous polyorganosiloxanes according to the invention can be synthesized starting from long chained epoxy precursors.

The invention claimed is:

1. A polyorganosiloxane compound comprising:
a) at least one polyorganosiloxane group,
b) at least one quaternary ammonium group, and
c) at least one terminal ester group,
wherein the polyorganosiloxane compound is a linear copolymer compound which comprises the above functional groups (a) and (b) in at least two repeating units, with at least part of the terminal groups being terminal ester groups (c) that result from the use of monofunctional organic acids as chain stoppers, and
wherein the molar ratio of the quaternary ammonium groups b) and the terminal ester groups c) is less than 100:15.

2. The polyorganosiloxane compound according to claim 1, further comprising
d) at least one polyalkylene oxide group.

3. The polyorganosiloxane compound according to claim 1, comprising at least one polyalkylene oxide group of the general formula:

-A-E-A'- wherein A and A' each are independently from each other selected from a single bond or a divalent organic group having up to 10 carbon atoms and one or more hetero atoms, and
E is a polyalkylene oxide group of the general formulae:

—[CH$_2$CH$_2$O]$_q$—[CH$_2$CH(CH$_3$)O]$_r$—[CH$_2$CH(C$_2$H$_5$)O]$_s$— with
q=0 to 200,
r=0 to 200,
s=0 to 200
and q+r+s =1 to 600.

4. The polyorganosiloxane compound according to claim 3, wherein A and A' are selected from the following groups
—CH$_2$CH(CH$_3$)—
—[CH$_2$CH$_2$O]$_q$—[CH$_2$CH(CH$_3$)O]$_r$—[CH$_2$CH(C$_2$H$_5$)O]$_s$—
—CH$_2$C(O)O—, —CH$_2$CH$_2$C(O)O—, —CH$_2$CH$_2$CH$_2$C(O)O—,
—OC(O)CH$_2$—, —OC(O)CH$_2$CH$_2$—, —OC(O)CH$_2$CH$_2$CH$_2$—,
—CH$_2$C(O)—, —CH$_2$CH$_2$C(O)—, —CH$_2$CH$_2$CH$_2$C(O)—,
—C(O)CH$_2$—, —C(O)CH$_2$CH$_2$—, —C(O)CH$_2$CH$_2$CH$_2$—,
—CH$_2$CH(OH)CH$_2$—, —O—CH$_2$CH(OH)CH$_2$—, —CH$_2$CH(OH)CH$_2$—O—,
—[CH$_2$CH$_2$O]$_q$—[CH$_2$CH(CH$_3$)O]$_r$—[CH$_2$CH(C$_2$H$_5$)O]$_s$—

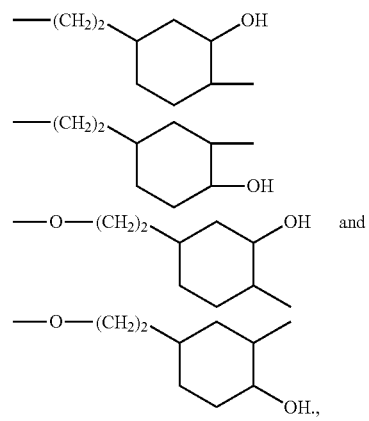

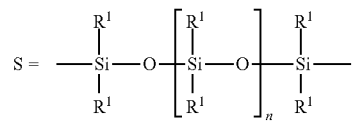

wherein the subscripts q, r and s are as defined.

5. The polyorganosiloxane compound according to claim 1, comprising at least one polyorganosiloxane group of the general formula:

—K—S—K—, with

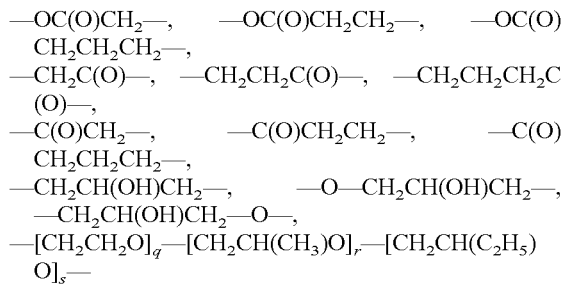

wherein R$^1$=C$_1$-C$_{22}$-fluoralkyl or aryl,
n=0 to 1000, and these can be identical or different if several S Groups are present in the polyorganosiloxane compound,
K= is a bivalent or trivalent straight chain, cyclic and/or branched C$_2$-C$_{40}$ hydrocarbon residue which is optionally interrupted by—O—, —NH—, trivalent N, —NR$^1$—, —C(O)—, —C(S)—, and optionally substituted with—OH, wherein R$^1$ is defined as above, whereby the residues K can be identical or different from each other.

6. The polyorganosiloxane compound according to claim 1, comprising at least one repeating unit comprising at least one quaternary ammonium group selected from the general formulas:

—N$^+$R$_2$—,

—N$^+$R$_2$-T-N$^+$R$_2$—, a saturated or unsaturated mono or diquaternary heterocycle of the formulae

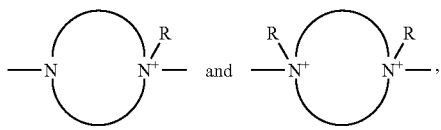

and
an aromatic ammonium heterocycle of the formula

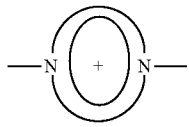

wherein R is selected from monovalent organic groups having up to 22 carbon atoms and optionally one or more heteroatoms, and wherein the free valencies at the nitrogen atoms are bound to carbon atoms, and T is selected from a divalent organic group having up to 20 carbon atoms and one or more hetero atoms.

7. The polyorganosiloxane compound according to claim 1, wherein the terminal ester groups are selected from the group of:
—OC(O)—Z
—OS(O)$_2$—Z
—OS(O$_2$)O—Z
—OP(O)(O—Z)OH
—OP(O)(O—Z)$_2$
wherein Z is selected from monovalent organic residues having up to 40 carbon atoms, optionally comprising one or more hetero atoms.

8. The polyorganosiloxane compound according to claim 1 of the general formulas (Ia) and (Ib):

$$M\text{-}Y\text{---}[\text{---}(N^+R_2\text{-}T\text{-}N^+R_2)\text{---}Y\text{---}]_m\text{---}[\text{---}(NR^2\text{-}A\text{-}E\text{-}A'\text{-}NR^2)\text{---}Y\text{---}]_k\text{-}M \quad (Ia)$$

$$M\text{-}Y\text{---}[\text{---}(N^+R_2\text{-}T\text{-}N^+R_2)\text{---}Y\text{---}]_m\text{---}[\text{---}(N^+R^2_2\text{-}A\text{-}E\text{-}A'\text{-}N^+R^2_2)\text{---}Y\text{---}]_k\text{-}M \quad (Ib)$$

wherein:
m is >0, preferred 0.01 to 100, more preferred 0.1 to 100, even more preferred 1 to 100, specifically 1 to 50, more specifically 1 to 20, even more specifically 1 to 10,
k is 0 or an average value of >0 to 50 preferred 1 to 20, more preferred 1 to 10,
M represents a terminal group, comprising terminal ester groups selected from
—OC(O)—Z
—OS(O)$_2$—Z
—OS(O$_2$)O—Z
—OP(O)(O—Z)OH
—OP(O)(O—Z)$_2$
wherein Z is selected from monovalent organic residues having up to 40 carbon atoms, optionally comprising one or more hetero atoms,
-A-E-A'-is such that A and A' each are independently from each other selected from a single bond or a divalent organic group having up to 10 carbon atoms and one or more hetero atoms, and
E is a polyalkylene oxide group of the general formulae:

—[CH$_2$CH$_2$O]$_q$—[CH$_2$CH(CH$_3$)O]$_r$—[CH$_2$CH(C$_2$H$_5$)O]$_s$— with
q=0 to 200,
r=0 to 200,
s=0 to 200
and q+r+s=1 to 600,
R$^2$ is selected from hydrogen or R, where R is selected from monovalent organic groups having up to 22 carbon atoms and optionally one or more heteroatoms
Y is a group of the formula:

—K—S—K— and -A-E-A'-or-A'-E-A-, with

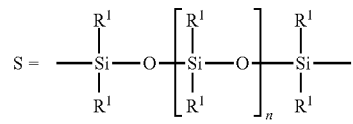

wherein R$^l$=C$_1$-C$_{22}$-alkyl, C$_1$-C$_{22}$-fluoralkyl or aryl,
n=0 to 1000, and these can be identical or different if several S Groups are present in the polyorganosiloxane compound,
K= is a bivalent or trivalent straight chain, cyclic and/or branched C$_2$-C$_{40}$ hydrocarbon residue which is optionally interrupted by —O—, —NH—, trivalent N,—NR$^1$—, —C(O)—, —C(S)—, and optionally substituted with —OH, wherein R$^1$ is defined as above, whereby the residues K can be identical or different from each other, and
A, A' and E are as defined above, and
T is selected from a divalent organic group having up to 20 carbon atoms and one or more hetero atoms.

9. The polyorganosiloxane compound according to claim 1, having protonated ammonium groups.

10. A process for the manufacture of the polyorganosiloxane compound according to claim 1, which comprises the reaction of
(i) at least one ditertiary diamine,
(ii) at least one amino-alkylating compound, comprising at least one diepoxide, and
(iii) at least one monofunctional organic acid,
wherein at least one compound among compounds (i) and (ii) comprises polyorganosiloxane structural units.

11. polyorganosiloxane compound as prepared by the process of claim 10.

12. The polyorganosiloxane compound according to claim 1, having a viscosity at 20° C. and a shear rate of 0.1 s$^{-1}$ below 100000 mPa·s.

13. An aqueous emulsiores comprising at least one polyorganosiloxane compound as defined in claim 1.

14. A method of surface treatment, comprising the step of applying the polyorganosiloxane compound as defined in claim 1, to the surface of a substrate.

15. The method of claim 14 wherein the polyorganosiloxane compound is present as one of a following compositions or formulations respectively:
cosmetic formulations for skin and hair care, selected from Rinse-off and Leave-on conditioners, shampoos, styling gels, sprays, and pump sprays; formulations for polishing for the treatment and outfitting of hard surfaces; formulations for drying automobiles and other hard surfaces; formulations for initial outfitting of textiles and textile fibers; softener formulations comprising in addition non-ionogenic or anionic/non-ionogenic or cationic or betaine surfactants for application during or after washing textiles; laundry formulations for textile washes based upon non-ionic or anionic/non-ionic or cationic or betaine surfactants or formulations for preventing or reversing textile crumpling.

16. A polyorganosiloxane composition, comprising:
A) at least one polyorganosiloxane compound, comprising
   a) at least one polyorganosiloxane group,
   b) at least one quaternary ammonium group, and
   c) at least one terminal ester group, wherein the polyorganosiloxane compound (A) is a linear copolymer compound which comprises the above functional groups (a) and (b) in at least two repeating units, with at least part of the terminal groups being terminal ester groups (c) that result from the use of monofunctional organic acids as chain stoppers, and
B) at least one polyorganosiloxane compound, comprising at least one terminal ester group, different from compound A).

17. The polyorganosiloxane composition according to claim 16 wherein the weight ratio of compound A) to compound B) is less than 90:10.

18. The polyorganosiloxane composition according to claim 16 wherein in compound A) the molar ratio of the quaternary ammonium groups b) and the terminal ester groups c) is less than 100:10.

19. A polyorganosiloxane compound consisting essentially of:
   a) at least one polyorganosiloxane group,
   b) at least one quaternary ammonium group, and
   c) at least one terminal ester group,
   wherein the polyorganosiloxane compound is a linear copolymer compound which comprises the above functional groups (a) and (b) in at least two repeating units, with at least part of the terminal groups being terminal ester groups (c) that result from the use of monofunctional organic acids as chain stoppers, and
   wherein the molar ratio of the quaternary ammonium groups b) and the terminal ester groups c) is less than 100:15.

20. The polyorganosiloxane compound according to claim 19, further consisting essentially of:
   d) at least one polyalkylene oxide group.

\* \* \* \* \*